(12) United States Patent
Porikli et al.

(10) Patent No.: US 8,781,183 B2
(45) Date of Patent: Jul. 15, 2014

(54) ENHANCED VISUALIZATIONS FOR ULTRASOUND VIDEOS

(75) Inventors: Fatih M. Porikli, Watertown, MA (US); Teng-Yok Lee, Columbus, OH (US)

(73) Assignee: Mitsubishi Electric Research Laboratories, Inc., Cambridge, MA (US)

(*) Notice: Subject to any disclaimer, the term of this patent is extended or adjusted under 35 U.S.C. 154(b) by 705 days.

(21) Appl. No.: 12/639,777

(22) Filed: Dec. 16, 2009

(65) Prior Publication Data

US 2011/0007952 A1  Jan. 13, 2011

Related U.S. Application Data

(60) Provisional application No. 61/165,369, filed on Mar. 31, 2009.

(51) Int. Cl.
*G06K 9/00* (2006.01)
*G06T 7/00* (2006.01)
*G06F 19/00* (2011.01)

(52) U.S. Cl.
CPC .............. *G06T 7/0012* (2013.01); *G06F 19/321* (2013.01)
USPC .......................................................... 382/128

(58) Field of Classification Search
CPC ............ G06T 2207/10132; G06T 7/20; G06T 7/0012
USPC ............................................................. 382/128
See application file for complete search history.

(56) References Cited

U.S. PATENT DOCUMENTS

| 4,907,973 | A  | * | 3/1990  | Hon .............................. 434/262 |
| 5,797,846 | A  | * | 8/1998  | Seyed-Bolorforosh et al. ............................. 600/447 |
| 8,357,100 | B2 | * | 1/2013  | Eriksen et al. ................. 600/538 |
| 2004/0184647 | A1 | * | 9/2004  | Reeves et al. ................. 382/131 |
| 2009/0326349 | A1 | * | 12/2009 | McGonigle et al. .......... 600/323 |
| 2010/0061596 | A1 | * | 3/2010  | Mostafavi et al. ............ 382/107 |
| 2010/0111386 | A1 | * | 5/2010  | El-Baz .......................... 382/128 |

* cited by examiner

*Primary Examiner* — Sheetal R Rangrej
(74) *Attorney, Agent, or Firm* — Dirk Brinkman; Gene Vinokur

(57) ABSTRACT

A method estimates a pattern of change of a patient, specifically a change in the respiration pattern. An ultrasound video is segmented into groups of pictures (GOPs). Pixels from the first GOP are used to initialize a change model. Based on the change model, a change pattern for a next GOP is estimated, and the change model is changed to fit the change pattern. The estimating and the updating are repeated until a termination condition is reached.

13 Claims, 7 Drawing Sheets

ENHANCED VISUALIZATIONS FOR ULTRASOUND VIDEOS

RELATED APPLICATION

This patent application claims priority to Provisional Application 61/165,369, "Enhanced Visualizations for Ultrasound Videos," filed by Fatih M. Porkli et al. on Mar. 31, 2009, incorporated herein by reference.

FIELD OF THE INVENTION

The invention relates generally estimating a change pattern, and more particularly to estimating and visualizing the change pattern from a video acquired with ultrasonography.

BACKGROUND OF THE INVENTION

The respiration pattern of a patient can be used to optimize particle beam radiation therapy. The intent is estimate the pattern that corresponds to "breathing in" and "breathing out." The estimation should be dynamic and real time to control the energy of the particle beam so that a maximal dosage is delivered to any abnormal tissue, while the dosage to normal tissue is minimized.

Instead of the respiration information, a change pattern of the depicted target tissue can also employed to achieve the adaptive gating of such therapy systems. For instance, the current state e.g. ultrasound image of the tumor is compared to the safe radiation state i.e. the ultrasound image where the tumor is in the desired position. In case these states match the radiation is applied. However, a change in these states indicates the tumor may not be in the desired location, thus the radiation should not be applied.

An evaluation of the accuracy of the estimation is also important, although not straightforward. In theory, if the exact signal is available, then statistical quantities, such as Euclidean distance, cross-correlation or phase-correlation between the exact signal and the estimated pattern, can be determined. However, the exact signal is not available during the treatment.

As a result, the only way to evaluate the change pattern is by visualization. As the change pattern is estimated from an ultrasonic video, the signal pattern should be visually compared with the video to measure the correlation. This visualization should reveal whether the expected pattern of "breathing" in the video matches the estimated pattern, or whether the pattern is deviant in case of respiration.

That is, radiotherapy technicians need an effective visualization to detect any deviant change in the respiration pattern during the treatment, and make a decision whether the therapy should be continued or terminated.

It is also desired to provide an effective visualization to determine whether the phases and frequencies of the estimated change pattern match the motion of organs as seen in the video. Given a 2D video and a change pattern signal, the goal is to highlight the periodicity of the underline motion in the video, and efficiently comparing the correlation between the motion in the 2D video and the 1D signal. However, a long video is time-consuming to watch.

Video surveillance applications can visualize events by representing the video as a static spatio-temporal volume. After low level image features, such as gradients or motion flows, have been extracted from the volume, convectional volume rendering techniques used to enhance those features to visualize the underline events. For example, direct volume rendering, with transfer functions that assign high transparencies to static region can hide the background in a scene, and flow visualization techniques such as glyphs or streamlines integrals can be applied to visualize the extracted motion flow. The common goal in those techniques is visualizing the motion in the environment.

If the ultrasonic video is watched as conventional animation, then the user cannot precisely reveal the periodicity, especially the duration of cycle in the pattern and the shift of phase that are common in medical imaging, because the phases and frequencies of respiration are dynamic. It is also difficult to check the correlation between the moving 2D pattern and the 1D signal over longer time intervals. For instance, the video and the signal can be positively correlated in one part of the video, but negatively correlated in another part. The user cannot immediately recall and detect such a difference when the phase of the correlation is continuously delayed.

Conventional video representations utilize a 2D display screen as the X, Y coordinate space, and changes the image (frames) over time, while the plotting of a 1D signal $y=f(t)$ often utilizes the 2D display screen as the T, Y coordinate space. This difference makes it non-intuitive to compare the 2D spatial video and the 1D temporal signal pattern, especially when the video frame is changing. If a video with thousands of frames is represented as a long volume, then only a part of the video can be displayed on the screen at any time in the Y, T coordinate space.

Therefore, it is desired concurrently visualize the 2D video and the 1D change signal.

SUMMARY OF THE INVENTION

The change pattern of a patient can be utilized to optimize radiation therapy using a particle beam. The embodiments of the invention provide a method for estimating the change pattern of the patient from an ultrasonic video. By using graphic processer units (GPU), the change pattern can be estimated and visualized in real time.

The embodiments provide visualization strategies to reveal a correlation between an estimated change pattern and the ultrasonic video. The change pattern forms a signal, i.e. a 1D discrete time or time series signal. The visualizations include on-line interfaces to detect abnormalities. An off-line method provides a static overview of a long video, such that the correlation, frequencies, and phase shifts of both the change pattern and the video can be detected.

However, the exact change pattern of the patient is not available during the treatment. Therefore, we acquire a video of the patient using ultrasonography. Then, the particle beam can be controlled to maximize the dosage delivered to abnormal tissues, while the dosage to normal tissue is minimized.

Specifically, a method estimates a pattern of change of a patient, specifically a change in the respiration pattern. An ultrasound video is segmented into groups of pictures (GOPs). Pixels from the first GOP are used to initialize a change model. Based on the change model, a change pattern for a next GOP is estimated, and the change model is changed to fit the change pattern. The estimating and the updating are repeated until a termination condition is reached.

DETAILED DESCRIPTION OF THE PREFERRED EMBODIMENT

The embodiments of our invention provide a method and system for estimating a change pattern of a patient. The change pattern can be used to a control a particle beam during radiation therapy and other applications where the interaction between the change and the therapy is a critical component. The embodiments also provide a method for visualizing the pattern, and correlating the pattern with an ultrasound video. It is to be understood that the term "patient" can generally refer to any living organism that breathes. It is also noted that other organs, such as the heart, that periodic patterns can also be visualized.

System

Figure 1:
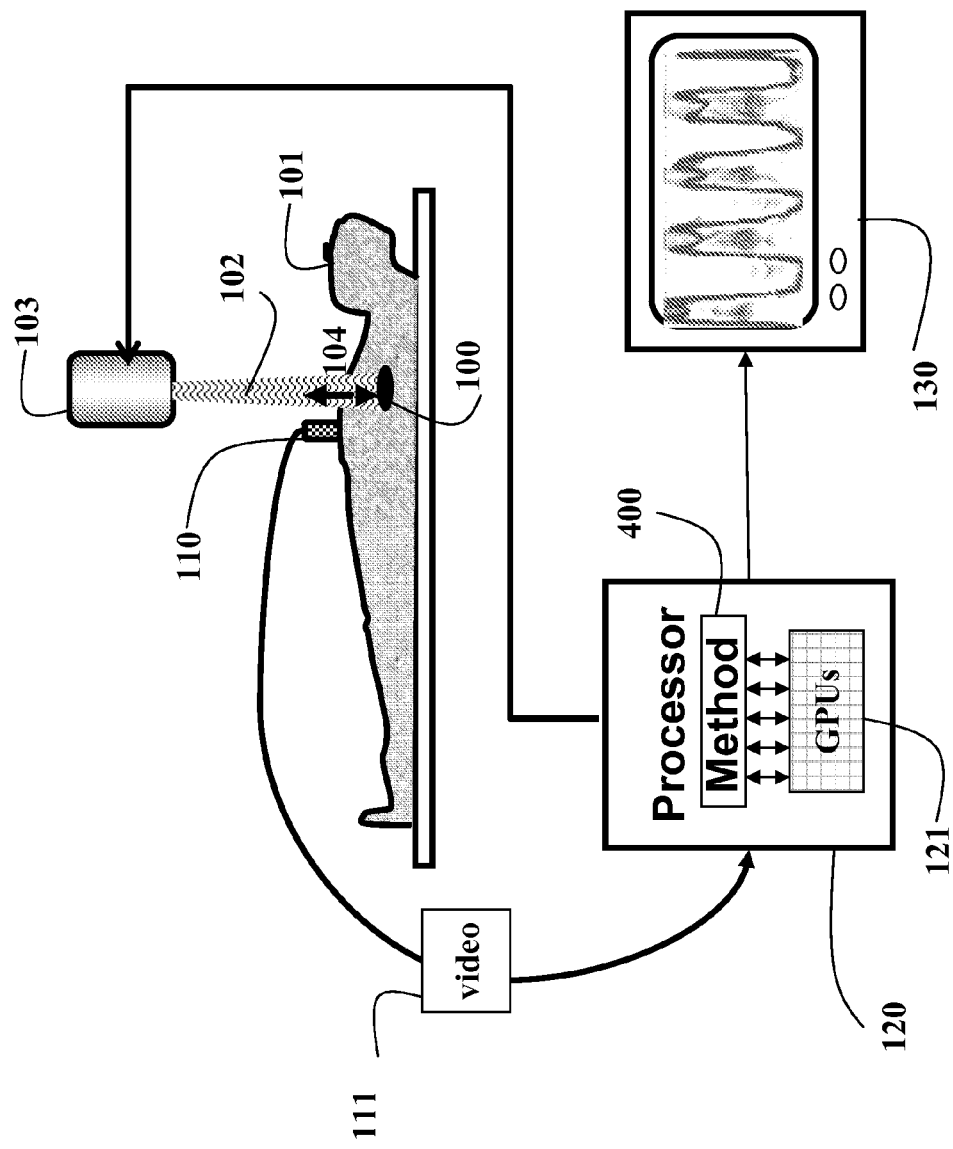
FIG. 1 is a block diagram of a system and method for estimating a change pattern according to embodiments of the invention.

FIG. 1 shows a radiation therapy arrangement that uses embodiments of our invention. Abnormal tissue 100 of a patient 101 is treated with a particle beam 102 generated by a teletherapy device 103 while the patent is breathing 104. An ultrasonic sensor 110 produces time series data in the form of an ultrasound video 111. A processor 120 performs steps of a method 400 for estimating the change pattern. The result can be rendered on a display device for a user, e.g., a radiotherapy technician. The result can also be used to control the particle beam.

Analyzes

We analyze a spectrum of the pixel intensities over time interval t in the video to detect the change pattern. By updating the pattern over time, the method can track the dynamics of the change. We use a processor that includes graphic processing units (GPU) 121 to analyze the spectrum in real time.

The visualization includes on-line (real time) and off-line visualization interfaces. The on-line interface allows the user to monitor the radiation therapy by comparing the change signals and the video frames. The user can align the 1D signal with the video frames to maximize the correlation between the underline motion in the video and the change signal. The user can quickly compare the correlation in the same 2D coordinate system, and detect when the correlation fails. The off-line visualization provides an overview of the change signal, and the ultrasound video.

The video is projected to 2D space to generate small multiples of the pattern corresponding to the same stage in the change. The user can quickly identify dissimilar patterns, and determine the periodicity and phase of the change signal.

Change Estimation

Figure 2:
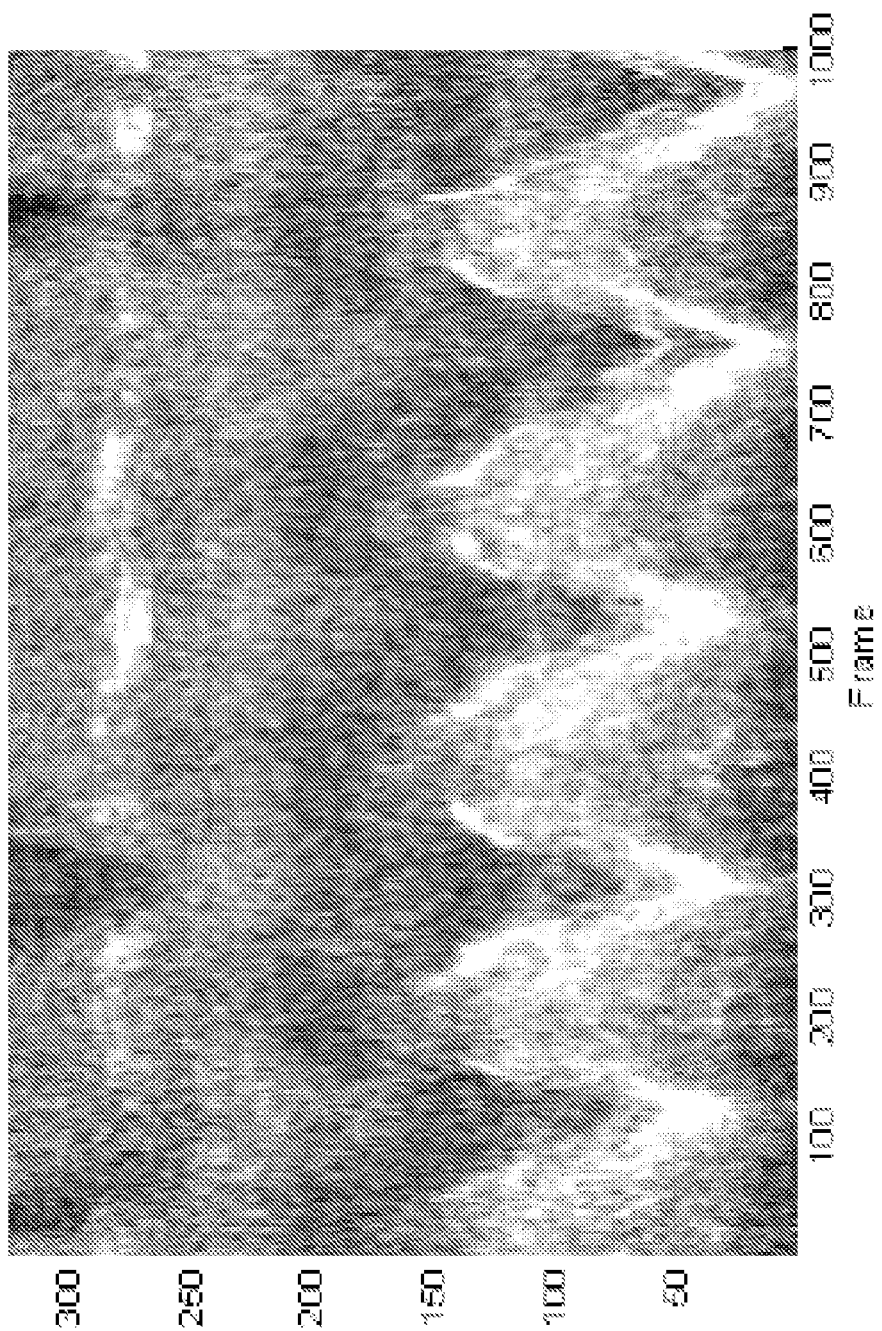
FIG. 2 is an image of a slice of a 3D ultrasonic video volume in Y and T coordinate space according to embodiments of the invention.

The intuition behind our method is shown in FIG. 2. FIG. 2 shows cascaded rows in the middle of the first 512 video frames of the ultrasound video. By representing the horizontal dimension as the frame indices, quausi-sinusoid patterns are visible along the horizontal time direction, suggesting that there are pixels whose intensities over time should be correlated to the change signal.

We design our method based on this intuition. The method selects a set of pixels whose intensities over a finite number of time intervals are similar to that of the change signal.

Terminologies

Sets of successive video frames are automatically segmented into groups of pictures (GOPs). The number of video frames in a GOP can be set to any fixed or adaptively changing number. To take advantage of the fast Fourier transform (FFT) based techniques, it is preferred to set the number to powers of two, i.e., $2^n$.

The GOPs can overlap in time up to all frames (except the oldest one i.e., the first frame in the GOP). Alternatively, the GOPs do not overlap. The amount of the overlap determines the computational complexity and the smoothness of the estimated signals. More overlap between the GOP's result in smoother estimates, however such an overlap also requires more computational resources, than no overlap.

A frame of the GOP can be the whole input frame or a specified region of interest (ROI) in the input frame. The ROI can be tracked between the frames or correspond to the same location in each input frame.

The intensity of a pixel over time corresponds, in part, to the change pattern signal. Thus, the frequencies and spectrum of the signal corresponds to the pixel intensities over time.

Figure 3:
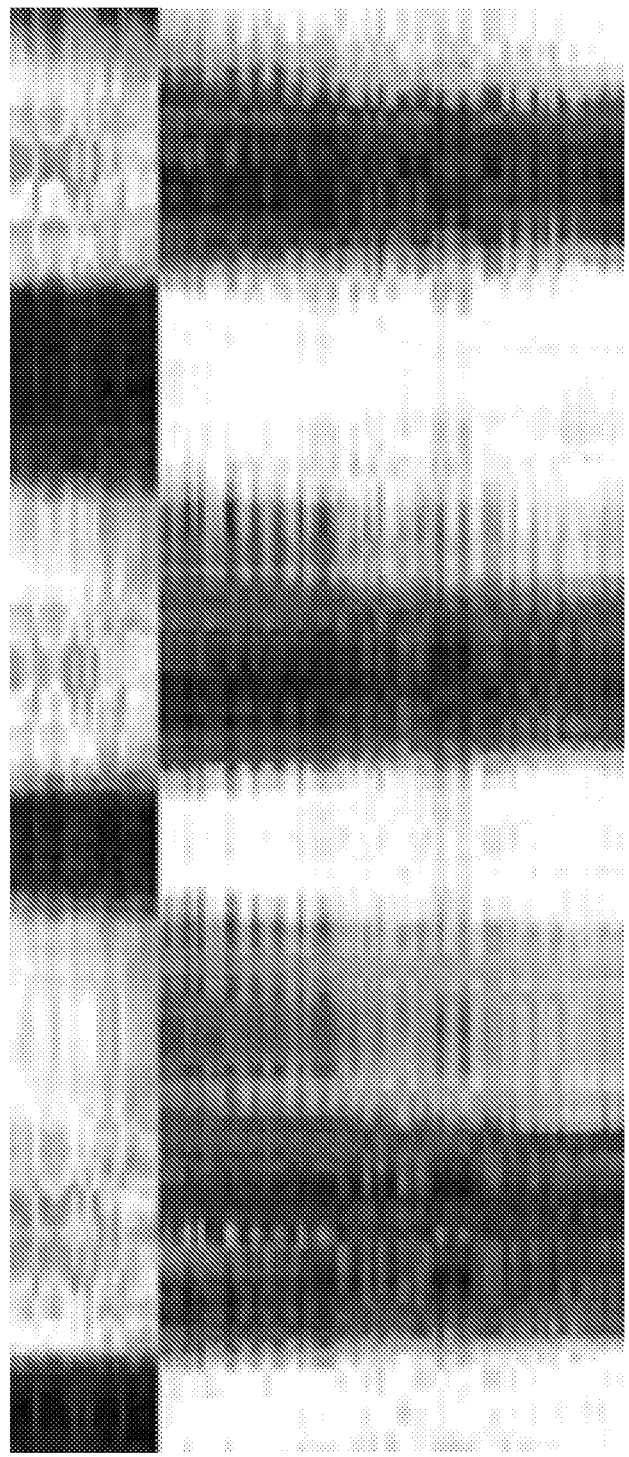
FIG. 3 is an image of opposed phases of change band energies according to embodiments of the invention.

The change pattern we consider in the following description is due to the respiration motion. The frequency range of respiration is a respiration band, which is from 10 to 18 cycles per minute (the range can be as low as 5 and as high as 30 depending the age, health, etc of the persons). For the signal, the energy in the respiration band is the respiration band energy (RBE). As shown in FIG. 3, the signal is categorized into two sets with opposed phase, and thus the magnitude of the average signal is small.

Given the average spectrum of a set of signals of the same lengths, the frequency with a largest magnitude in the respiration band is defined as the predominant respiration frequency of the set of signals. The phase of the predominant respiration frequency in the average spectrum is defined as the predominant respiration phase of the set of signals. The types of the patterns over time can include the harmonic motion and deformation of the tissues as observed in the video. In the following section, we will use "pattern" to refer to all the activities in the video.

Method

Figure 4:
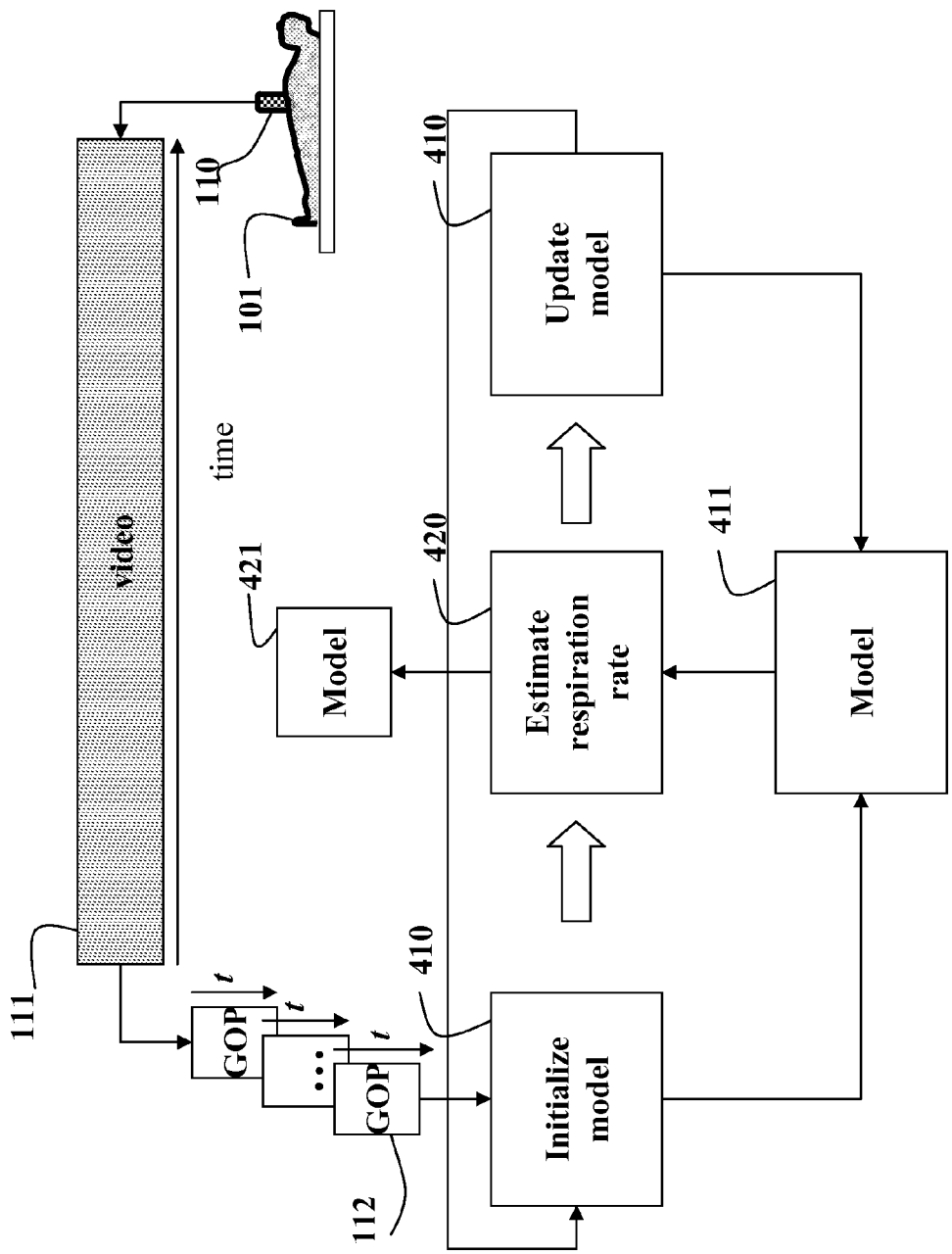
FIG. 4 is a block diagram of a method for estimating a change pattern according to embodiments of the invention.

As shown in FIG. 4, the method 400 initializes 410 a change (for breathing motion, a respiration) model 411 from the first GOP 112 of the video 111. A model is a collection of the pixels within a GOP that is assumed to represent the underlying periodic (breathing-like) motion pattern. In other words, our model is a subset of pixels, which may change at each GOP, within the image region.

Based the model, the method estimates 420 the change (respiration) pattern 421 for next GOP.

The model is updated 430 to fit the change (respiration) dynamics of the patient for this GOP.

Then, the method repeated the estimation and updating for the next GOP, until a termination condition is reached, e.g., the end of the video.

Initialization

We consider a respiration model in the following description. However, the method covers all periodic changes, hence we call it a change model.

The ROI is selected as the whole frame. It can also be selected by the user a region in the image that depicts the desired periodic changes, for instance the respiration pattern.

The change model is initialized based on a set of pixels whose intensities in the first GOP contain apparent periodic patterns in frequencies corresponding to respiration. The RBE of each pixel in the GOP is determined. The pixels with RBEs greater than a threshold are selected as candidates to model the respiration, where the number of candidate pixels and the threshold can be specified by the user. Instead of thresholding, a certain number of pixels having the highest RBEs can also be selected.

The intensities of the candidate pixels contain patterns in frequencies corresponding to the respiration. Thus, an average signal can represent the respiration of the patient.

The magnitude of the average signal of all candidate pixels can be small because the phases of the candidate pixels can be opposed to each other, as shown in FIG. 3. FIG. 3 shows that the signals with highest RBE from the first GOP. Because the phases of the two groups of signals are opposed to each other, their magnitudes are canceled during the averaging, causing an unstable signal because the ultrasound video is often noisy. Therefore, only the candidate pixels with similar phases are selected to model the respiration.

One naïve option would groups the pixels using a conventional clustering process, such as K-mean clustering, here K=2. However, K-mean processes are iterative and time-consuming. Therefore, a simpler processed is used to cluster the pixels. First, after the average spectrum of the candidate pixels has been determined, the predominant respiration frequency of all candidate pixels is determined as the frequency with a largest magnitude among the respiration band in this average spectrum.

Next, among the phases in the predominant respiration frequency of all candidate pixels, the dominant phase is determined. Our process uses a constructs a polar histogram for the phases. The phase of the bin with the largest count is selected as the dominant phase. Then, the pixels with phases in this bin are selected to model the respiration.

Estimation

For each of the following GOP, the corresponding respiration signal is estimated as the averaged intensity of the candidate selected pixels in the frame. The selected pixels are used until the last frame in the next GOP has been processed.

Update

When the last frame of a next GOP has been reached, a new set of pixels is selected from this GOP to update the change model. The average signal of the new-selected pixels contain apparent periodic patterns corresponding to the respiration, and form a continuous transition from the estimated signal in previous GOPs to that in the next GOP.

To generate a continuous phase transition of the respiration signal, the predominant respiration frequency and the predominant respiration phase of the previously selected pixels in this next GOP are determined. Next, the pixels are sorted according to their RBE in this GOP. The pixels are then processed in a high to low order of the RBE.

For each pixel, if the difference between the phase of the predominant respiration frequency and the predominant respiration phase is smaller than a threshold, then the pixel is selected. The selection terminates after a specified number of pixels have been selected.

Implementation

The predominant performance bottleneck of our method is the calculation of the spectrum for each pixel. To accelerate our method, we perform the steps on the GPUs in real time.

Visualization

The goal of our visualizations is to reveal the correlation between the motion and deformation of tissue in the ultrasound video, and the estimated respiration signal. The on-line visualization can effectively compare the observable pattern in the video and the estimated respiration signal. The off-line visualization generates an overview to reveal both the correlation between the video and the respiration signal in a single image, and the frequency and phase shift of the respiration signal.

On-Line Visualization Interface

A naïve solution simultaneously displays the video and the respiration signal in different windows. However, switching the focus of the user between the windows is ineffective because the video frame and the respiration signal often use different 2D coordinate spaces, thus, establishing a comprehensive visual perception is difficult.

Our on-line visualization interface has multiple display windows to present various information extracted from the ultrasound video. In one window, we concurrently displays both the video and the respiration signal, where the respiration signal and the video frames is superimposed in such a way that it maximizes the correlation between the respiration signal and the periodic motion in the video.

Figure 5:
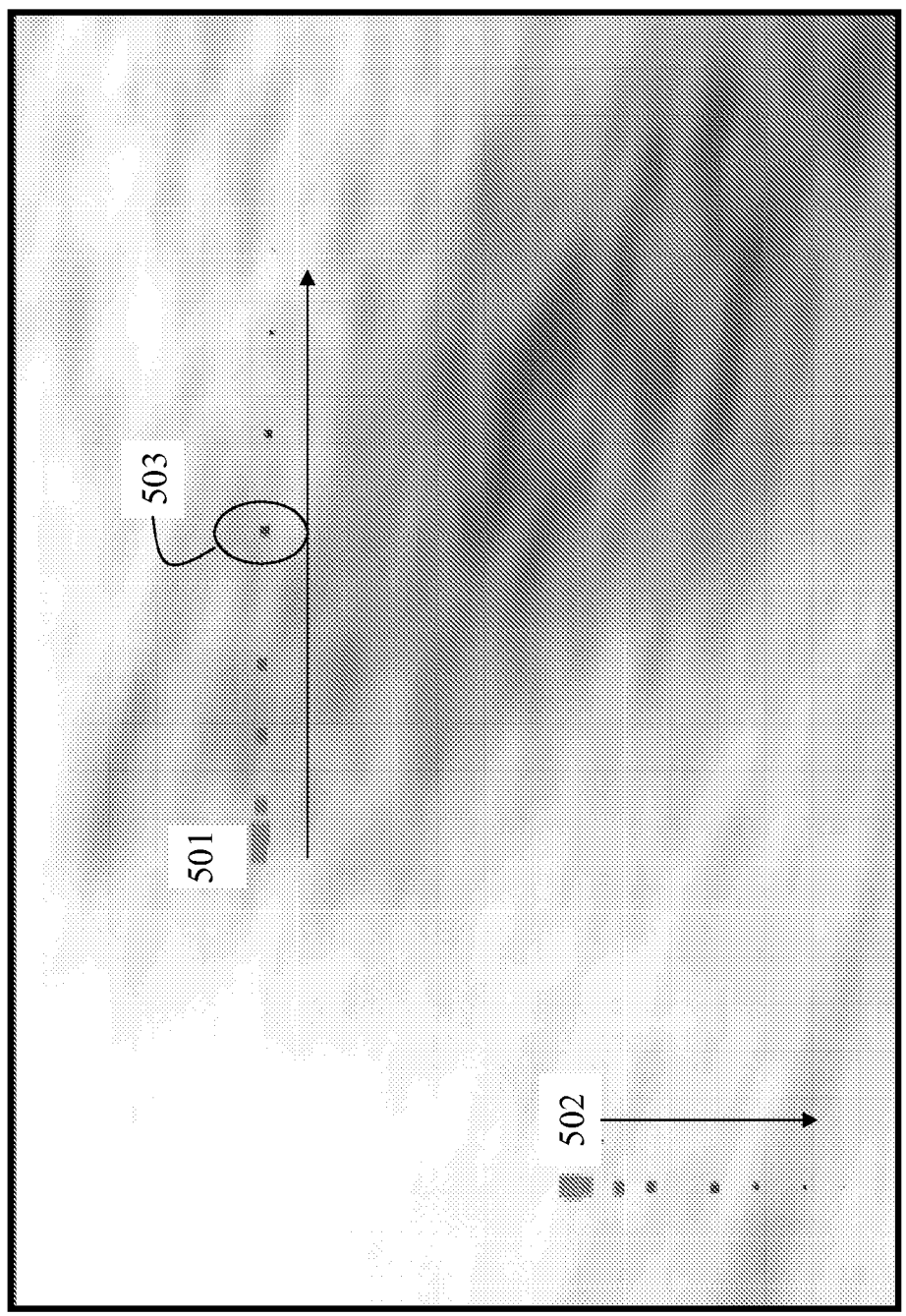
FIG. 5 is an image of an on-line visualization interface according to embodiments of the invention.

As shown in FIG. 5, in one of the displays, the user can specify an axis, for instance, along the direction of the predominant apparent periodic motion in the video frame. We call this axis as the signal axis 501. Subsequently, the magnitude of the respiration signal is plotted along the signal axis such that the previous signals are shown in a smaller scale and different color to indicate the direction of the motion. The two ends of the signal axis can be linearly mapped to the value range of the signal. Each time interval t of the signal can be linearly plotted axis according to its value.

Each time interval is plotted as a blotch 503 whose radius is inversely proportional to the distance between the time to a current time step. This display window enables defining multiple signal axes, e.g. 501 and 502 to improve the perception. As shown in FIG. 3, two signal axes (501-502) are displayed over the frame. The interface also displays the RBE for each pixels. In other words, the RBE and the pixel intensities in the original ultrasound frame are blended, e.g. by multiplying, in the display window. This augments the visual understanding of the most informative pixels that are used to estimate the breathing motion.

To make the interface more effective, we show the respiration pattern across multiple video frames in a single displayed image. For each video frame, we sample the pixel intensities along the signal axis into a single column, and append this column to the end of an image. By displaying the image with the corresponding signal, the user can visualize the periodic motion and the signal across several frames in a single view, which can be useful to detect deviant respiration.

Figure 6A:
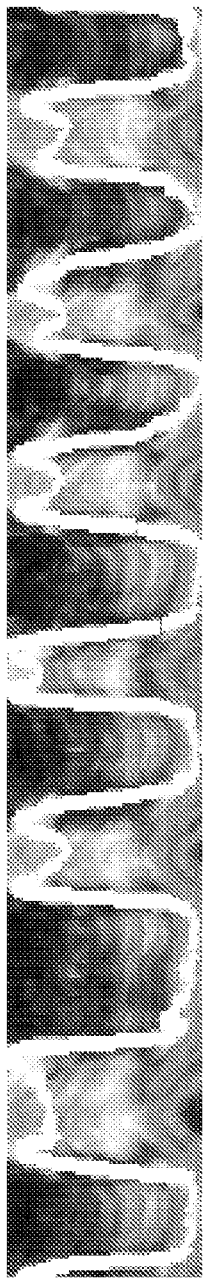
FIGS. 6A-6 images of an odd-line visualization interface according to embodiments of the invention.
Figure 6B:
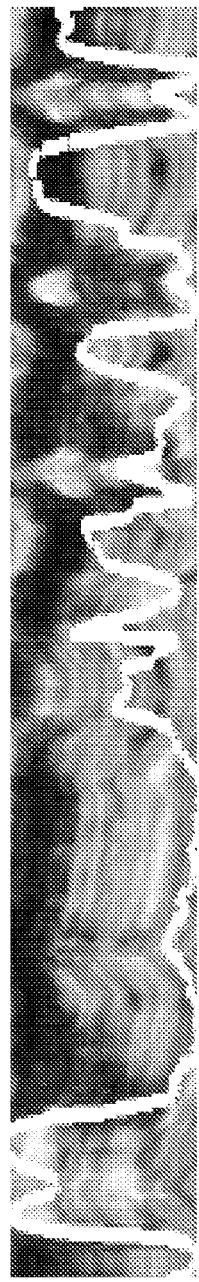
Figure 6C:
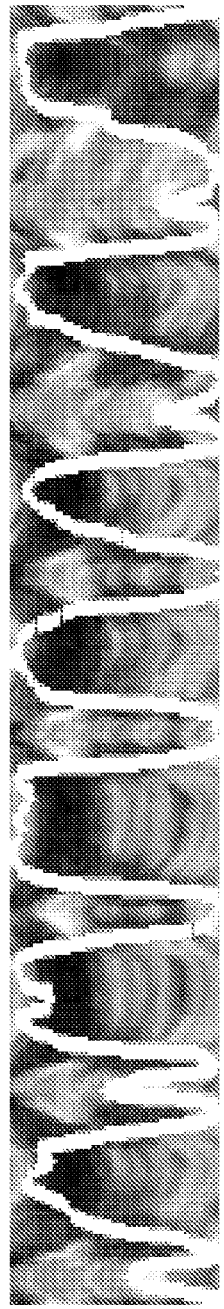

FIGS. 6A-6C show three different results of this extended visualization. The video and the signal axes for the three figures are the same, although at different time intervals.

FIG. 6A presents the image after the user has aligned the signal axis with the motion. It shows that the periodicity of the estimated signal is highly positively correlative with the motion. This is surprising because the estimation of the respiration does not rely on the spatial distribution of the pattern in a video frame.

FIG. 6B show a case where the pattern is aperiodic in the image, and the estimated signal is unstable.

FIG. 6C shows that the correlation between the signal and the pattern is negative or inverted, which is in contrast to the condition in FIG. 6A. The cases in both FIG. 6B-6C are deviant and require user interaction during the treatment.

Figure 7:
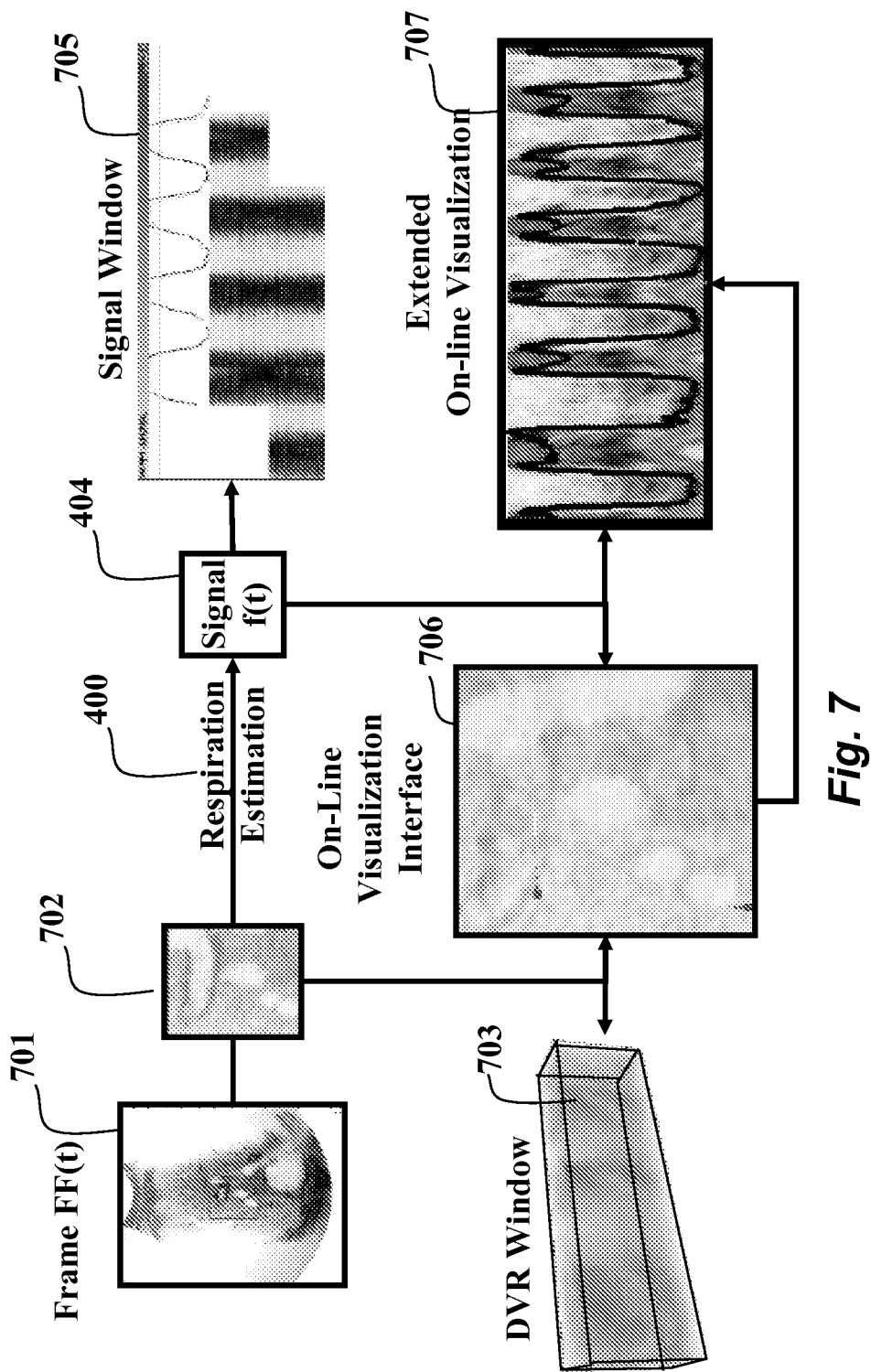
FIG. 7 is a block diagram of a visualization method according to embodiments of the invention.

FIG. 7 shows an overview of our visualization method. The input video frame is displayed in a frame window 701. A user specified region of interest (ROI) 702 is extracted. The ROIs of the multiple frames are combined into a spatio-temporal data as a video volume 703 and displayed in the display window 706.

The respiration estimator method 400 estimates the respiration signal f(t) 704 from the ROI. The estimated signal and the selected pixels are displayed in the signal window 705.

Then, the ROI and the estimated signal are correlatively visualized in the on-line visualization interface 706. The signal and the pixel intensities along the time-signal in the on-line visualization interface are displayed in the extended visualization interface 707 to correlatively visualize the periodic pattern in the video and the signal.

Off-Line Visualization

The off-line visualization renders a static image as an overview of both the ultrasound video and the estimated respiration signal. In addition to revealing the correlation between the video and the signal, the overview also reveals the frequencies and phases of the respiration signal.

First, the entire video is treated as a 3D volume, which is then projected to a 2D image that contains the same periodic pattern as in the video. Next, the 2D image is weighted according to the respiration signal, which is equivalent to filtering image patterns corresponding to the peaks of the signal. Finally, the weighted image is wrapped around the display boundaries to effectively display the entire video with less compression and distortion of the filtered patterns.

This projection aligns the x-axis of the image with the temporal dimension of the video. In other words, the number of columns of this projected image is proportional to the number of video frames, and the temporal trends in the video are displayed vertically from left to right.

The projection of the y-axis can have different options to determine the content of each column. Given a column, its content can be obtained by cutting a slice parallel to the time axis through the video volume, or using the sampled pixel intensities over time along the signal-axis. It can be also obtained via conventional volume rendering techniques such as maximal intensity projection (MIP) or direct volume rendering (DVR) by making the z-axis of the coordinates of the sensor 110 perpendicular to the time axis, and the x-axis of the sensor parallel to the time-axis.

For a long video sequence, this rendering cannot be completed in a single pass. Therefore, the video volume is rendered as a series of images, and registered to form a long image. Orthogonal projection is used during the rendering to avoid the distortion due to the perspective projection.

The projected image is weighted according to the respiration signal. First, the value of the signal is linearly normalized to a range [0, 1]. Each row in the image is multiplied by weighted the value of the corresponding time step in the normalized signal. This weighting can highlight the image columns whose corresponding signals are near the peak and surpass other image columns. The successive highlighted image columns contain the projection of the patterns in the video.

By visually comparing the similarity among those patterns, the user can easily observe whether the correlation between the signal and the motion in the video is consistent. The length of each pattern, and the distances between successive patterns also reflect the frequency of the estimated signal.

Because the number of columns is proportional to the number of time intervals, the image can be too long, causing a less effective visualization because each pattern can only cover limited space on the display. To guarantee that each pattern can cover sufficient space on the display screen, the long image is wrapped around the display boundaries. The wrapping can efficiently utilize the 2D screen space and intuitively reveal the phases of the signal.

If a clear diagonal appears in the wrapped image between a range of time steps, then the frequency is constant during the period.

Although the invention has been described by way of examples of preferred embodiments, it is to be understood that various other adaptations and modifications may be made within the spirit and scope of the invention. Therefore, it is the object of the appended claims to cover all such variations and modifications as come within the true spirit and scope of the invention.

We claim:

1. A method for estimating a pattern of change in respiration of a patient comprising the steps of:
    segmenting a video acquired of the patient into groups of pictures (GOPs), each GOP is formed by successive video frames of the video acquired by an ultrasonic sensor;
    selecting a group of pixels from a first GOP as a change model, wherein intensities of the pixels in the first GOP form a periodic pattern in frequencies corresponding to the respiration of the patient;
    estimating, based on the change model a change pattern for a next GOP, wherein the change pattern represents the pattern in the respiration;
    updating the change model to fit the change pattern; and
    repeating the estimating and the updating until a termination condition is reached, wherein steps of the method are performed by a processor.

2. The method of claim 1, wherein the GOPs overlap in time.

3. The method of claim 1, wherein the initializing is based on a set of pixels in the first GOP whose intensities contain apparent periodic patterns in frequencies corresponding to respiration.

4. The method of claim 3, wherein a frequency range of the respiration is a respiration band and an energy in the respiration band is a respiration band energy (RBE), and further comprising:
    determining, for each pixel in the GOP, the RBE; and
    selecting the pixels with RBEs greater than a threshold and similar phases for initializing the change model.

5. The method of claim 3, wherein the change pattern, indicates a respiration pattern of the patient, and wherein a frequency range of the respiration pattern is a respiration band, and an energy in the respiration band is a respiration band energy (RBE), and further comprising:
    determining, for each pixel in the GOP, the RBE,
    selecting a number of pixels having the largest RBEs for initializing the change model.

6. The method of claim 3, further comprising:
    grouping the selected pixels in the initialized change model into similar phases.

7. The method of claim 3, further comprising:
    constructing a polar histogram of bins for the phases; and
    selecting the phase with the bin having a largest count as a dominant phase.

8. The method of claim 3, wherein the pattern is estimated as an averaged intensity of the selected pixels.

9. The method of claim 1, further comprising:
    controlling a particle beam according to the pattern.

10. The method of claim 1, further comprising
    visualizing the pattern as a signal in real time for each GOP.

11. The method of claim 10, wherein the visualizing concurrently displays the video and the signal in a single display window.

12. The method of claim 1, further comprising:
visualizing, off-line, the entire video and the pattern as a signal.

13. The method of claim 12, further comprising:
weighting frames of the video according to the signal.

* * * * *